(12) United States Patent
Nikolskiy et al.

(10) Patent No.: US 6,633,789 B1
(45) Date of Patent: *Oct. 14, 2003

(54) EFFIICIENT DATA REPRESENTATION OF TEETH MODEL

(75) Inventors: Sergey Nikolskiy, Moscow (RU); Elena Pavloskaia, San Francisco, CA (US); Huafeng Wen, Redwood Shores, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,721

(22) Filed: May 23, 2000

Related U.S. Application Data

(63) Continuation-in-part of application No. 09/506,419, filed on Feb. 17, 2000.

(51) Int. Cl.[7] .......................... G06F 19/00; A61C 19/10
(52) U.S. Cl. ..................... 700/98; 700/97; 700/118; 433/2; 433/24
(58) Field of Search .................. 700/97, 98, 118–120, 700/163; 433/2, 24

(56) References Cited

U.S. PATENT DOCUMENTS

| | | |
|---|---|---|
| 4,793,803 A | 12/1988 | Martz |
| 5,338,198 A | 8/1994 | Wu et al. |
| 5,590,248 A | 12/1996 | Zarge et al. |
| 5,605,459 A | 2/1997 | Kuroda et al. |
| 5,607,305 A | 3/1997 | Andersson |
| 5,882,192 A | 3/1999 | Bergersen |
| 6,015,289 A | 1/2000 | Andreiko et al. |
| 6,044,170 A | 3/2000 | Migdal et al. |
| 6,044,309 A | 3/2000 | Honda |
| 6,049,743 A | 4/2000 | Baba |
| 6,205,243 B1 | 3/2001 | Migdal |
| 6,212,442 B1 * | 4/2001 | Andersson et al. ......... 700/161 |
| 6,217,334 B1 | 4/2001 | Hultgren |
| 6,227,850 B1 | 5/2001 | Chishti et al. |
| 6,244,861 B1 * | 6/2001 | Andreiko et al. ............... 433/3 |
| 6,250,918 B1 * | 6/2001 | Sachdeva et al. ............. 433/24 |
| 6,315,553 B1 * | 11/2001 | Sachdeva et al. ........... 433/213 |
| 6,350,119 B1 * | 2/2002 | Jordan et al. ................ 206/396 |
| 6,350,120 B1 * | 2/2002 | Sachdeva et al. ............. 433/24 |
| 6,431,870 B1 * | 8/2002 | Sachdeva ..................... 433/213 |
| 6,463,351 B1 * | 10/2002 | Clynch ........................ 700/163 |
| 6,471,512 B1 * | 10/2002 | Sachdeva et al. ............. 433/24 |

FOREIGN PATENT DOCUMENTS

| WO | WO98/32394 A1 | 7/1998 |
|---|---|---|

OTHER PUBLICATIONS

Doyle, "Digital Dentistry" *Computer Graphics World* (Oct. 2000) pp. 50–52, 54.

(List continued on next page.)

*Primary Examiner*—Leo Picard
*Assistant Examiner*—Elliot Frank
(74) *Attorney, Agent, or Firm*—Townsend and Townsend and Crew LLP; Bao Tran, Esq.

(57) ABSTRACT

A computer-implemented method generates a computer model of one or more teeth by receiving as input a digital data set of meshes representing the teeth; selecting a curved coordinate system with mappings to and from a 3D space; and generating a function in the curved coordinate system to represent each tooth.

30 Claims, 14 Drawing Sheets

OTHER PUBLICATIONS

Foley et al., "Fundamentals of Interactive Computer Graphics," Addison–Wesley Publishing Co., pp. 514–533.

Redmond et al., "Clinical Implications of Digital Orthodontics," *Am J. Orthodont. Dentofacial Orthopedics (2000) 117(2) pp. 240–242*.

Rogers, David F. and Adams, Alan, *Mathematical Elements for Computer Graphics*, MacGraw Hill Publishing Co., 2d Ed. pp. 426–450.

Watt et al., "Advanced Animation and Rendering Techniques Theory and Practice," Addison–Wesley Publishing Co, pp. 101–110.

W. Bohm, G. Farin, J. Kahmann, A *survey of curve and surface methods in CAGD*, Computer Aided Geometric Design 1 (1984), 1–60.

* cited by examiner

EFFIICIENT DATA REPRESENTATION OF TEETH MODEL

The current application is a continuation-in-part of U.S. application Ser. No. 09/506,419, filed on Feb. 17, 2000.

BACKGROUND

1. Field of the Invention

The invention relates generally to the field of orthodontics and, more particularly, to computer modeling of teeth.

2. Description of the Background Art

Tooth positioners for finishing orthodontic treatment are described by Kesling in the *Am. J. Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673–680; Cureton (1996) *J. Clin. Orthodon.* 30:390–395; Chiappone (1980) *J. Clin. Orthodon.* 14:121–133; Shilliday (1971) *Am. J. Orthodontics* 59:596–599; Wells (1970) *Am. J. Orthodontics* 58:351–366; and Cottingham (1969) *Am. J. Orthodontics* 55:23–31.

Kuroda et al. (1996) *Am. J. Orthodontics* 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

SUMMARY

A computer-implemented method generates a computer model of one or more teeth by receiving as input a digital data set of meshes representing the teeth; selecting a curved coordinate system with mappings to and from a 3D space; and generating a function in the curved coordinate system to represent each tooth.

Advantages of the system include one or more of the following. The system reduces the amount of data storage space required for storing and communicating teeth treatment information. By utilizing space more efficiently, the system reduces the cost of the system, improves the responsiveness of the system, and allows additional functionality to be implemented.

The system supports fast distance estimation from a point to the tooth surface. This capability is needed for rapid collision detection. It also supports smoothing of the tooth surface—for noise reduction. Such rapid collision detection may support real-time manipulation of the teeth for treatment. For example, a user moves a tooth, and the tooth stops when it came in contact with another tooth.

The system can also support patching small holes in the model of the teeth that may be generated during the taking impressions/negative impressions. The system also provides the user with a selectable range of precision in teeth geometry representation.

The system also allows visualization to be used to communicate treatment information in a computer-automated orthodontic treatment plan and appliance. The invention generates a realistic model of the patient's teeth without requiring a user to possess in-depth knowledge of parameters associated with patient dental data compression. Additionally, expertise in 3D software and knowledge of computer architecture is no longer needed to process and translate the captured medical data into a realistic computer model rendering and animation.

The invention allows teeth plan treatment to be generated and communicated in a simple and efficient manner. It also improves the way a treating clinician performs case presentations by allowing the clinician to express his or her treatment plans more clearly and gives a prospective patients an opportunity to visualize the facial changes associated with the proposed treatment. The invention allows multidisciplinary work teams to deal easily and efficiently with the treatment plan. Another major benefit is the ability to visualize and interact with models and processes without the attendant danger, impracticality, or significantly greater expense that would be encountered in the same environment if it were physical. Thus, money and time are saved while the quality of the treatment plan is enhanced.

The details of one or more embodiments of the invention are set forth in the accompanying drawings and the description below. Other features, objects, and advantages of the invention will be apparent from the description and drawings, and from the claims.

DETAILED DESCRIPTION

Systems and methods are provided for modeling teeth in creating a treatment plan. The systems and methods compress data associated with the teeth model to reduce the storage size and transmission time to a treating professional. Based on the treatment plan, the teeth can be incrementally moved using a plurality of discrete appliances, where each appliance successively moves one or more of the patient's teeth by relatively small amounts.

Figure 1A:
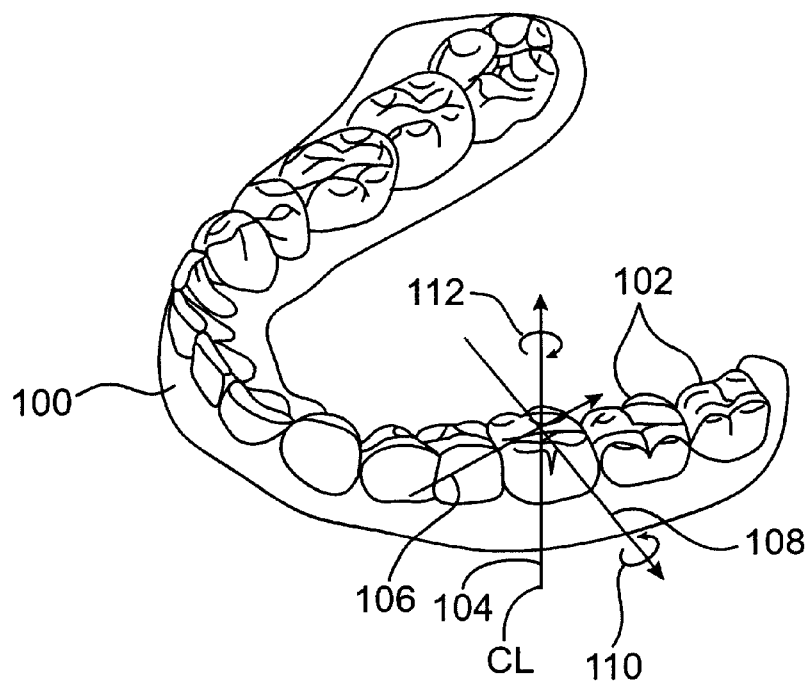
FIG. 1A illustrates a patient's jaw and provides a general indication of how teeth may be moved.

Referring now to FIG. 1A, a representative jaw 101 includes sixteen teeth, at least some of which are to be moved from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline (CL). Thus, all possible free-form motions of the tooth can be performed.

Figure 1B:
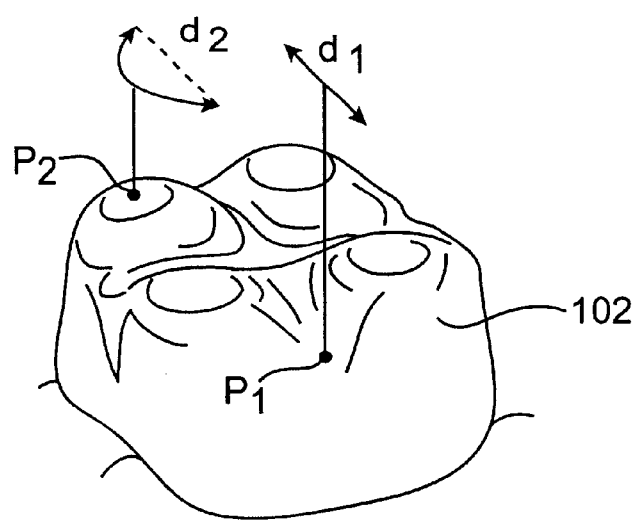
FIG. 1B illustrates a single tooth from FIG. 1A and defines how tooth movement distances are determined.

Referring now to FIG. 1B, the magnitude of any tooth movement is defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. In many situations, the maximum permissible movement of a point $P_i$ in any particular tooth is defined as the maximum linear translation of that point $P_i$ on the tooth that undergoes the maximum movement for that tooth in any treatment step.

One tool for incrementally repositioning the teeth in a patient's jaw is a set of one or more adjustment appliances. Suitable appliances include any of the known positioners, retainers, or other removable appliances which are used for finishing and maintaining teeth positions in connection with conventional orthodontic treatment. As described below, a plurality of such appliances can be worn by a patient successively to achieve gradual tooth repositioning. A particularly advantageous appliance is the appliance 100, shown in FIG. 1C, which typically comprises a polymeric shell having a cavity shaped to receive and resiliently reposition teeth from one tooth arrangement to another tooth arrangement. The polymeric shell typically fits over all teeth present in the upper or lower jaw. Often, only some of the teeth will be repositioned while others will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. The gums and the palette also serve as an anchor region in some cases, thus allowing all or nearly all of the teeth to be repositioned simultaneously.

Figure 1C:
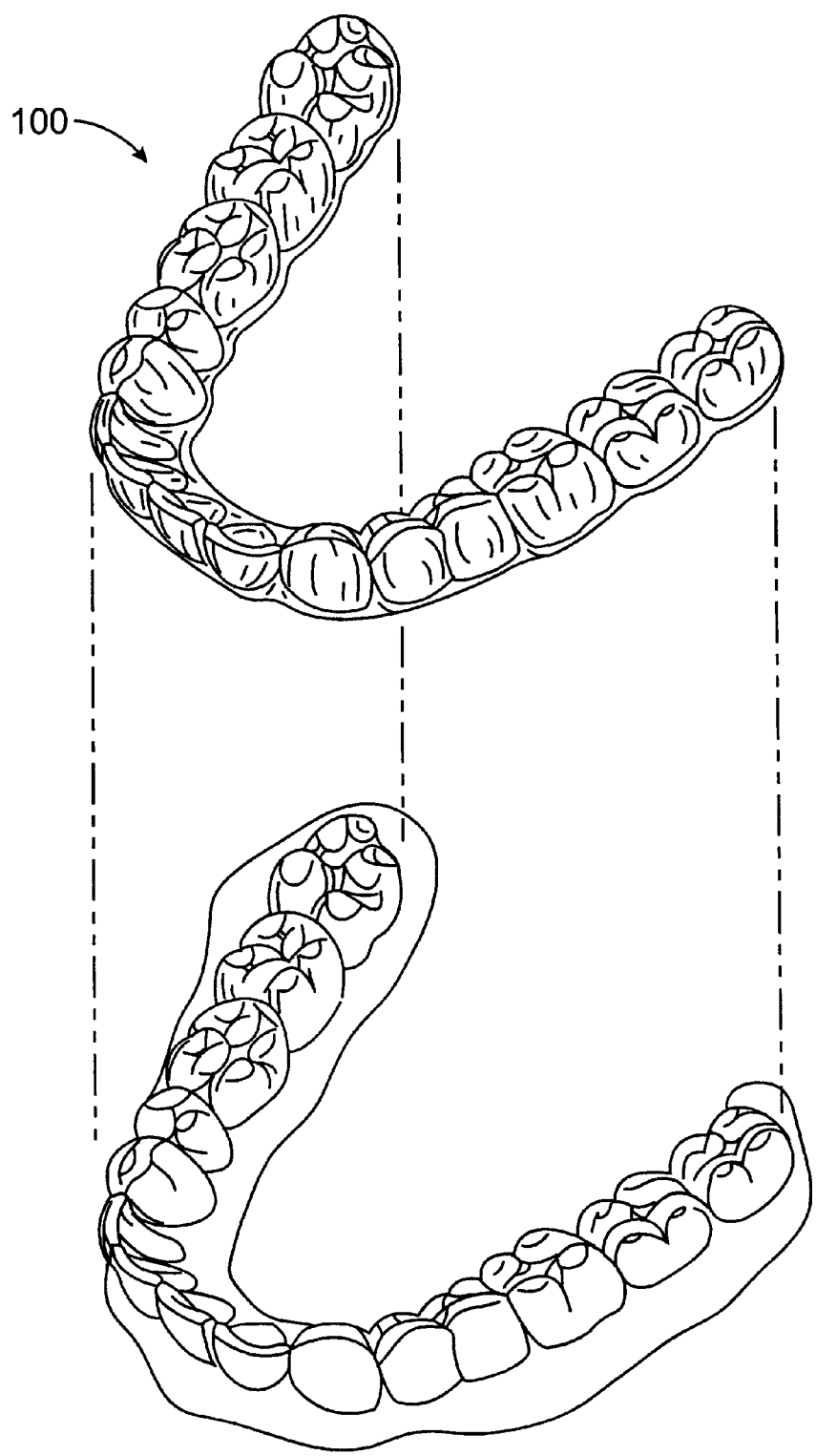
FIG. 1C illustrates the jaw of FIG. 1A together with an incremental position adjustment appliance.

The polymeric appliance 100 of FIG. 1C is preferably formed from a thin sheet of a suitable elastomeric polymeric, such as Tru-Tain 0.03 in. thermal forming dental material, marketed by Tru-Tain Plastics, Rochester, Minn. 55902. In many cases, no wires or other means are provided for holding the appliance in place over the teeth. In some cases, however, it is necessary to provide individual attachments on the teeth with corresponding receptacles or apertures in the appliance 100 so that the appliance can apply forces that would not be possible or would be difficult to apply in the absence of such attachments.

Figure 2:
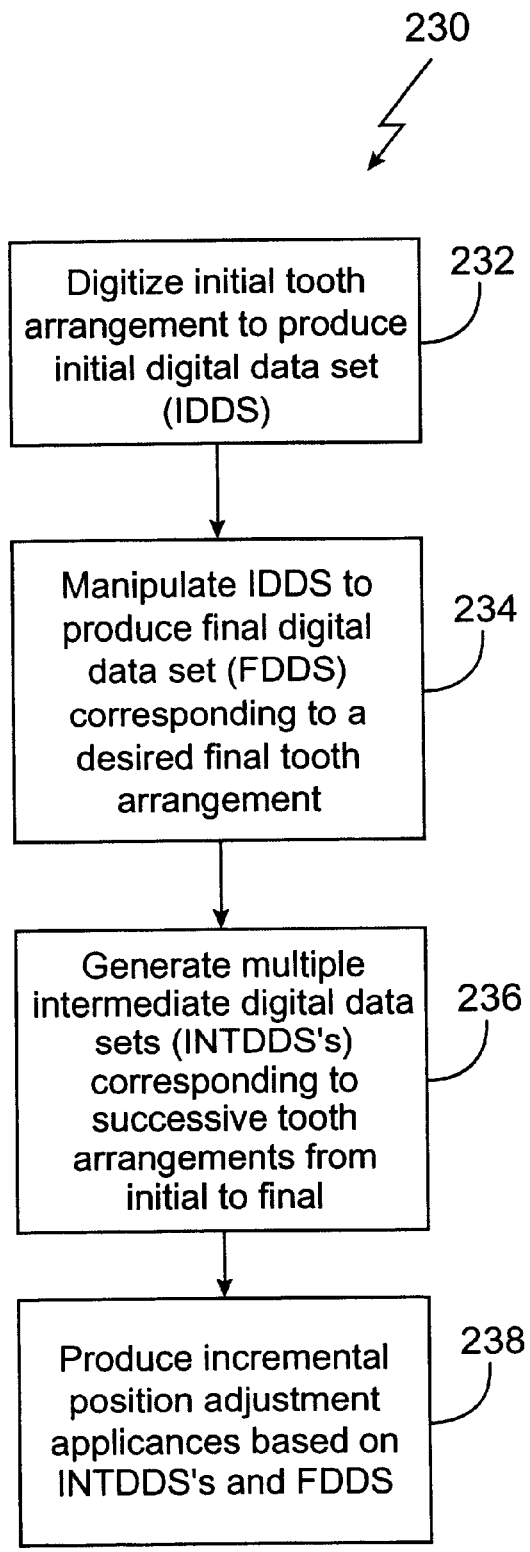
FIG. 2 is a block diagram illustrating steps for producing a system of incremental position adjustment appliances.

FIG. 2 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. More details on the contact or non-contact scanners are in commonly-owned and application Ser. No. 09/169,276, filed Oct. 8, 1998, the content of which is incorporated by reference.

A plaster cast of the patient's teeth is obtained by well known techniques, such as those described in Graber, *Orthodontics: Principle and Practice*, Second Edition, Saunders, Philadelphia, 1969, pp. 401–415. After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data. In addition to the 3D image data gathered by laser scanning or destructive scanning the exposed surfaces of the teeth, a user may wish to gather data about hidden features, such as the roots of the patient's teeth and the patient's jaw bones. This information is used to build a more complete model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying ankylose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

The IDDS is manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement that is customized to the patient's teeth, as discussed below. After applying the ideal model to the computer representation, and the position of the teeth is optimized to fit the ideal model. The ideal model may be specified by one or more arch forms, or may be specified using various features associated with the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

Figure 3:
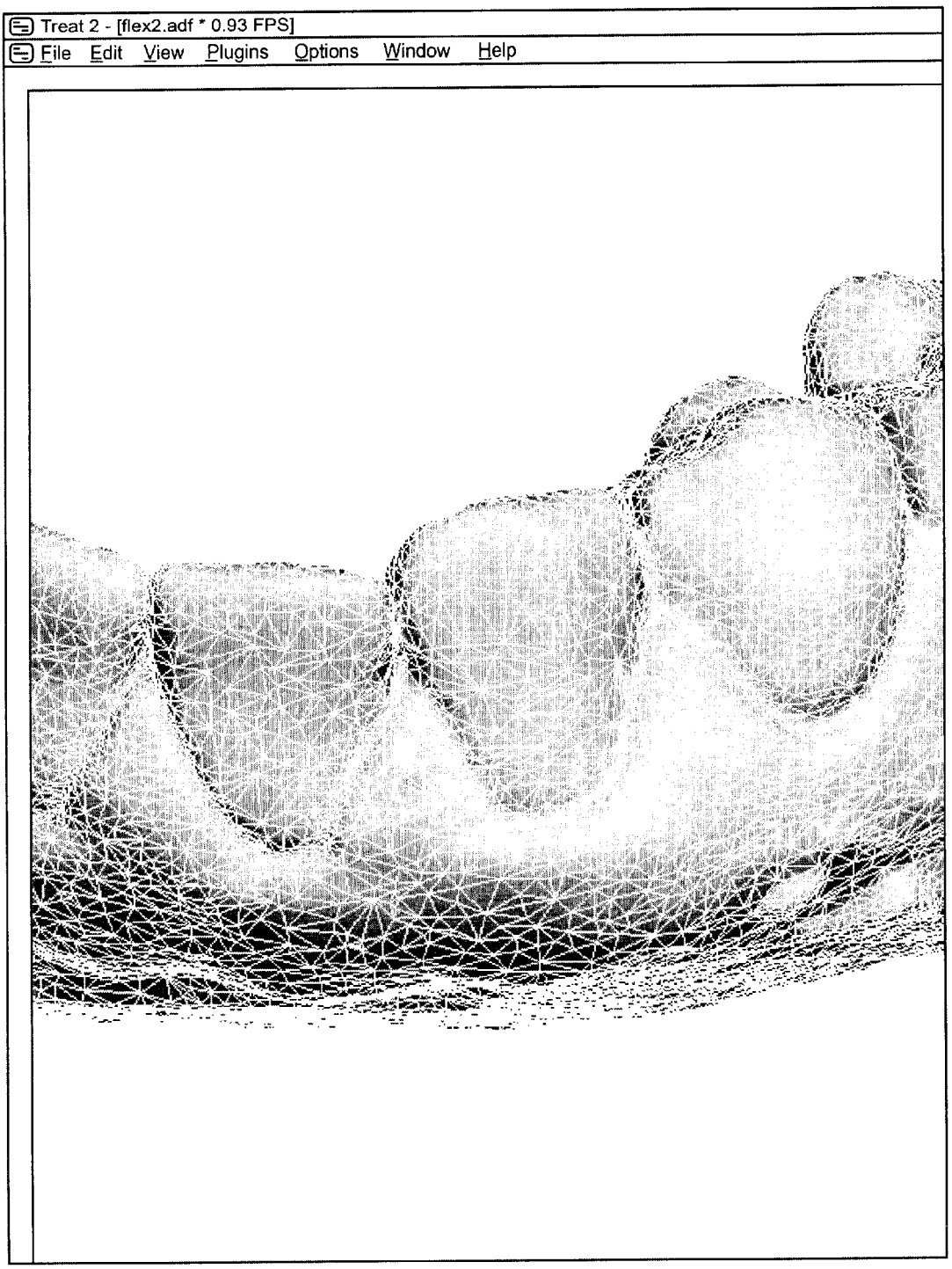
FIG. 3 is an illustration of a 3D model of teeth using triangular meshes.
Figure 3:
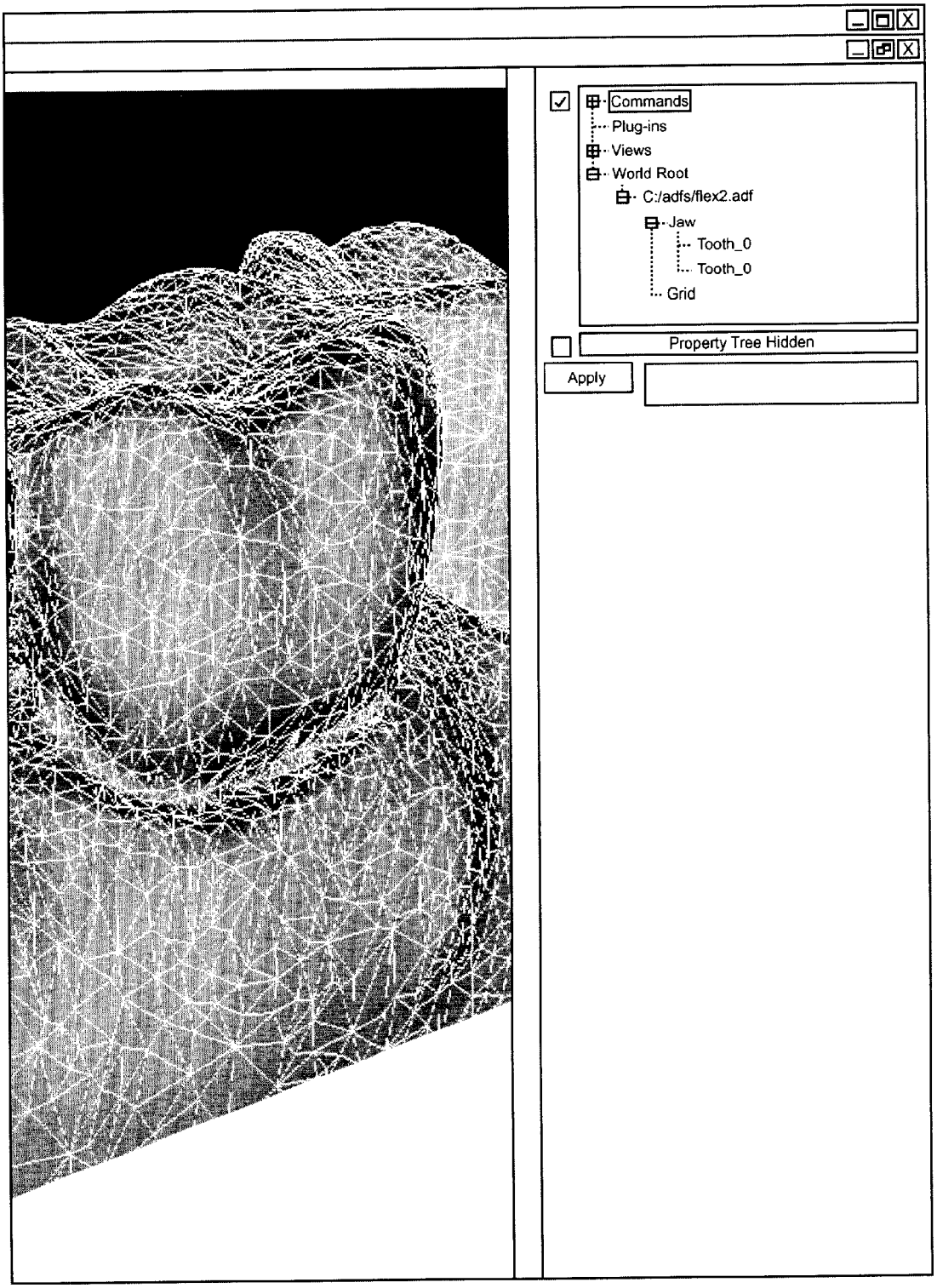

FIG. 3 shows one exemplary 3D surface model of the teeth. The surface topology of a 3D model of teeth on a jaw can be modeled as a set of polygons of appropriate sizes and shapes joined at their edges. The set of polygons defining the 3D object is referred to as the "model" or "mesh" for the 3D object. In one embodiment, the polygons are triangles. In this embodiment, a triangle mesh is a piecewise linear surface with triangular faces joined along their edges.

Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces. In one implementation, a marching cubes algorithm is applied to convert the voxels into a mesh, which can undergo a smoothing operation to reduce the jaggedness on the surfaces of the tooth model caused by the marching cubes conversion. One smoothing operation moves individual triangle vertices to positions representing the averages of connected neighborhood vertices to reduce the angles between triangles in the mesh.

The triangles in FIG. 3 form a connected graph. In this context, two nodes in a graph are connected if there is a sequence of edges that forms a path from one node to the other (ignoring the direction of the edges). Thus defined, connectivity is an equivalence relation on a graph: if triangle A is connected to triangle B and triangle B is connected to triangle C, then triangle A is connected to triangle C. A set of connected nodes is then called a patch. A graph is fully connected if it consists of a single patch. The processes discussed below keep the triangles connected.

Once a 3D model of the tooth surfaces has been constructed, models of the patient's individual teeth can be derived. In one approach, individual teeth and other components are "cut" using a cutting tool to permit individual repositioning or removal of teeth in or from the digital data. After the components are "freed", a prescription or other written specification provided by a treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Figure 4:
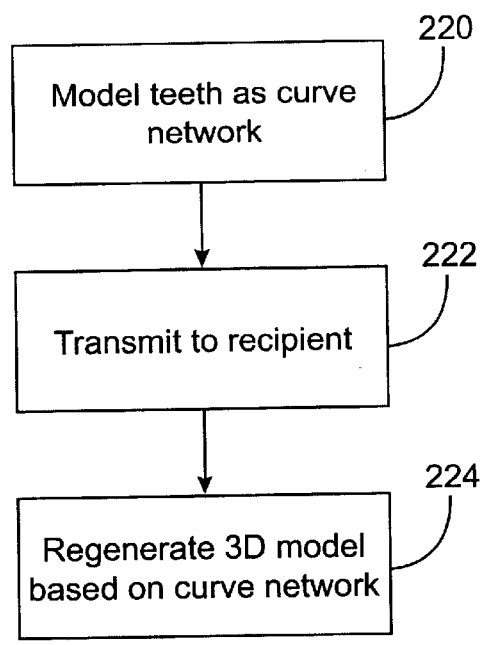
FIG. 4 shows a first embodiment of a system to represent a tooth model using a curved network.

FIG. 4 shows an embodiment of a process for communicating the 3D model of the teeth to the treating professional. Since realistic models have a large volume of data, the storage and transmission of the models can be expensive and time consuming. To reduce transmission problems arising from the large size of the 3D model, the system compresses the data associated with the model. In the embodiment of FIG. 4, the compression is done by modeling the teeth meshes as a curve network (step 220). Next, the curve network is transmitted to the treating professional (step 222). The curve network can be sent over a local area network (LAN) or a wide area network (WAN) such as the Internet. At the receiving end, once the curve network is received, the 3D model is reconstructed from the curve network for the treating professional to analyze (step 224).

Figure 5:
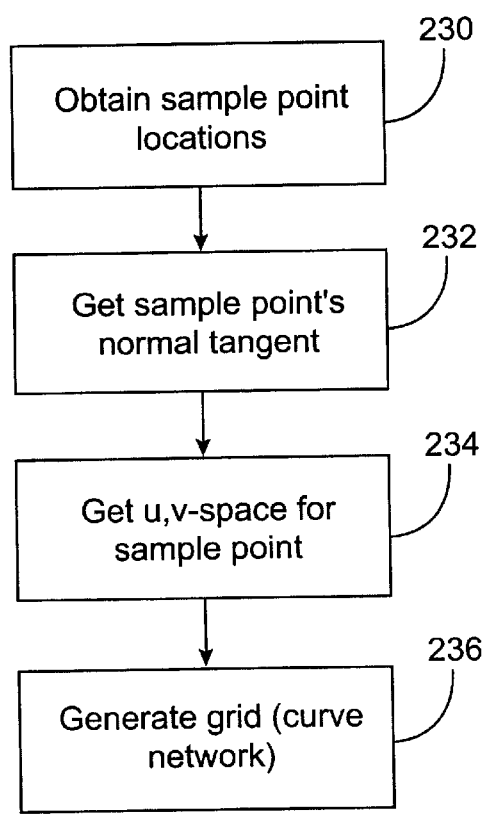
FIG. 5 is a flow chart illustrating a process for generating the curve network representative of a tooth.

The curve network generation of step 220 is shown in more detail in FIG. 5. First, the process of FIG. 5 obtains one or more sample points from the meshes of a tooth (step 230). Next, the process computes tangent values for the sample points (step 232). The sample points are converted into u, v-space (step 234). Finally, a grid or curve network is generated that satisfies the points in u, v-space (step 236). This is done by surface fitting the curve network to the original data.

In one embodiment of FIG. 5, data points are separated into groups. A U-curve with a U-knot vector is interpolated through each separate group. Next, one or more V-curves are generated by moving along each of the U-curves for a given knot value. The V-curve is formed by interpolating through these data points. The V-curves intersect the U-curves at points of constant u. A new set of U-curves that are constant in v is obtained by connecting points of constant v along the V-curves. A network of curves and its relationship to the original data points can then be generated. The only curves are drawn are either curves of constant u or constant v, and so the regions marked out by them are rectangular in u, v-space and can be represented at patches which also mark out rectangular domains in u, v-space. A patch representation is generated from the network to arrive at a full surface description. More details on the surface fitting are discussed in pages 101–110 of Alan Watt and Mark Watt, Advanced Animation and Rendering Techniques (Addison-Wesley Publishing Company, Menlo Park, Calif.).

Figure 6A:
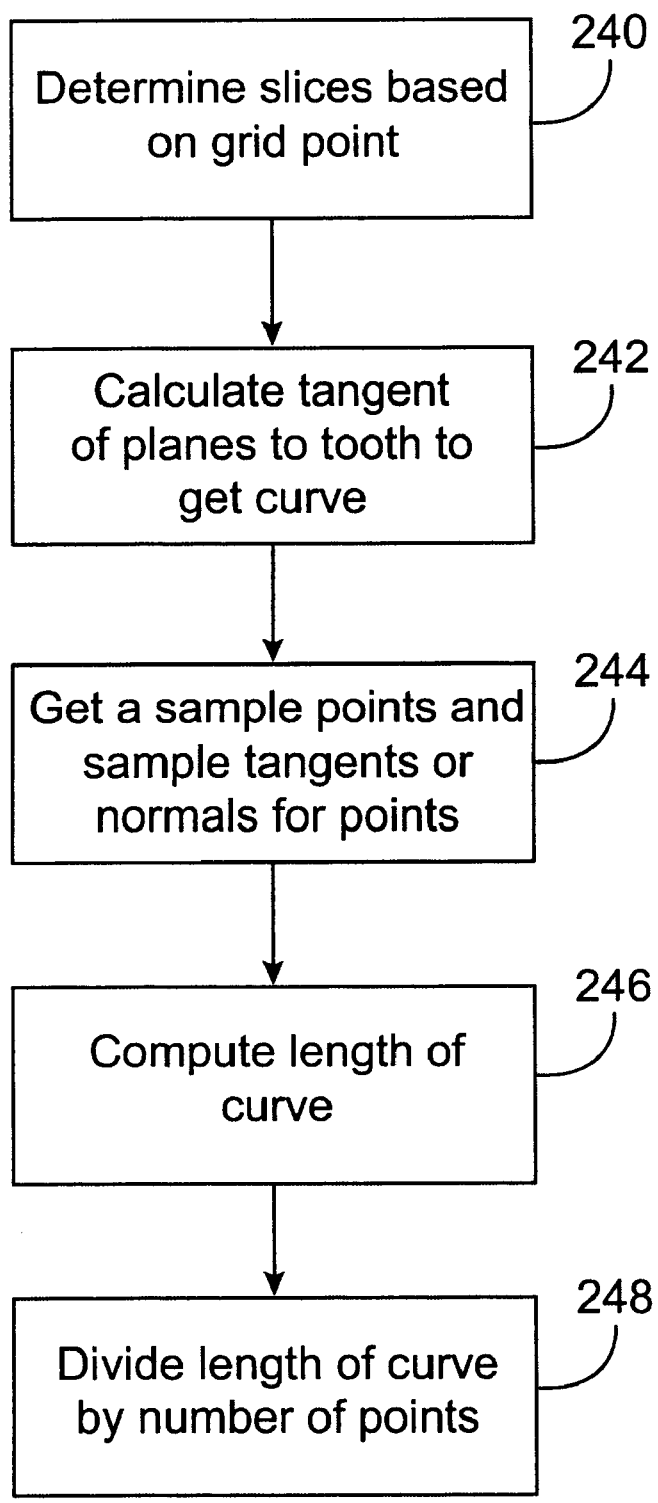
FIG. 6A is a flow chart illustrating a first process for generating an M×N network representative of a tooth.

FIG. 6A shows a flowchart for a process to create an M×N curve network associated with a tooth. First, the process determines M, the number of slices corresponding to meridian lines crossing the tooth (step 240). Next, the process calculates tangent values for a plurality of planes intersecting with the tooth to define a curve associated with one side of a slice (step 242). One or more sample points and sample tangent values for the sample points are selected (step 244) and the length of the curve is computed (step 246). Next, the process of FIG. 6 divides the length of the curve the N and generates points associated with the M×N curve network (step 248).

Each tooth is modeled as though it were a deformed ball. The curve network is a network of M meridian lines and N parallel lines. For each meridian line, a plane is selected to contain the meridian line. A series of points representing an intersection between the plane and the triangle mesh modeling a tooth is determined. The series of points represent a curve whose length is then determined. The length of the meridian is divided by N. If M is 20 and N is 20, a 20×20 grid of points is generated, each point being represented in 3-D. In this manner, M×N 3D points can be transmitted in place of the voluminous mesh representation of the teeth. To further reduce the size of the file, the coordinates of each point are stored using integer values rather than floating point values.

Figure 6B:
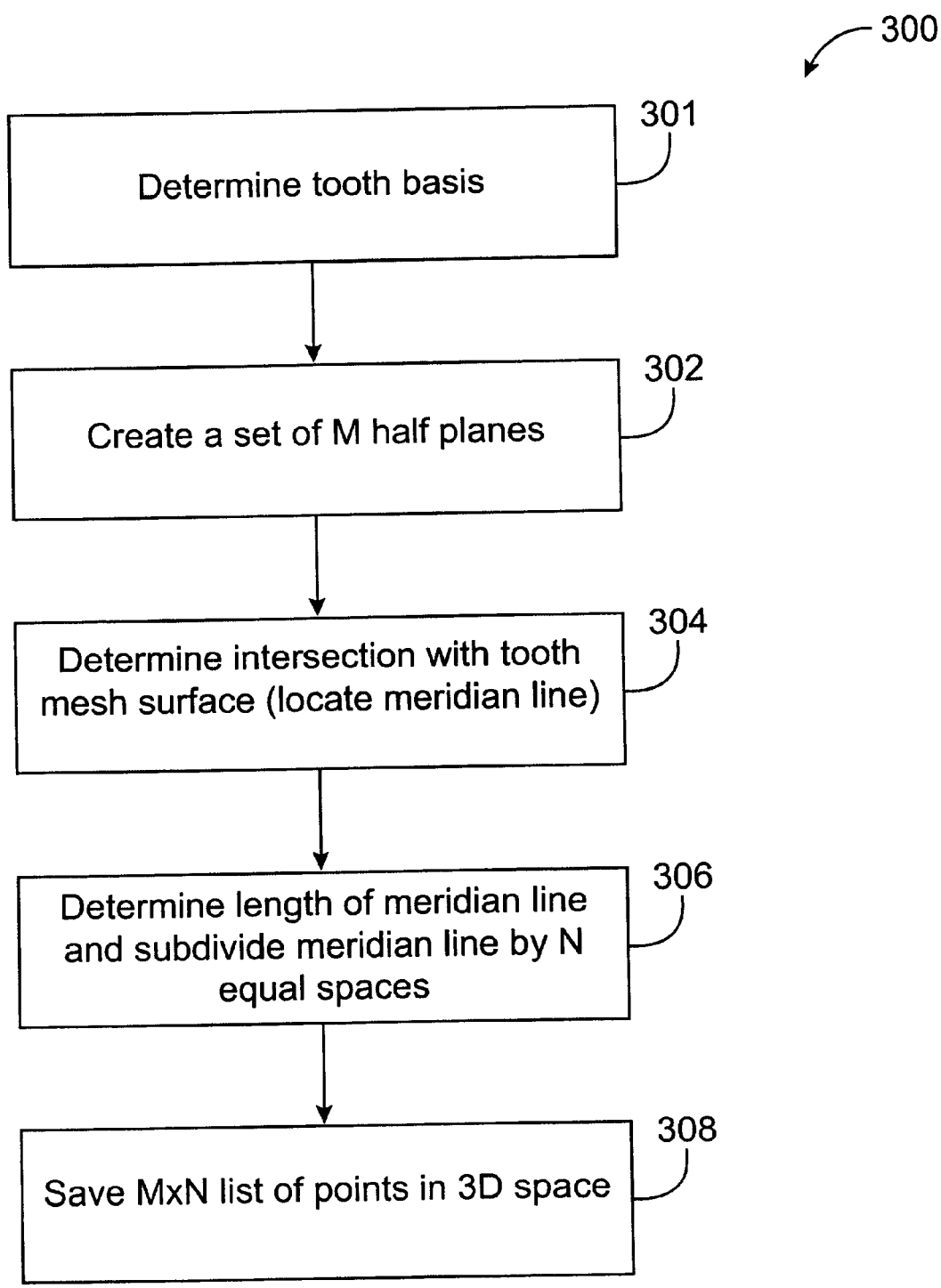
FIG. 6B is a flow chart illustrating a second process for generating an M×N network representative of a tooth.
Figure 6C:
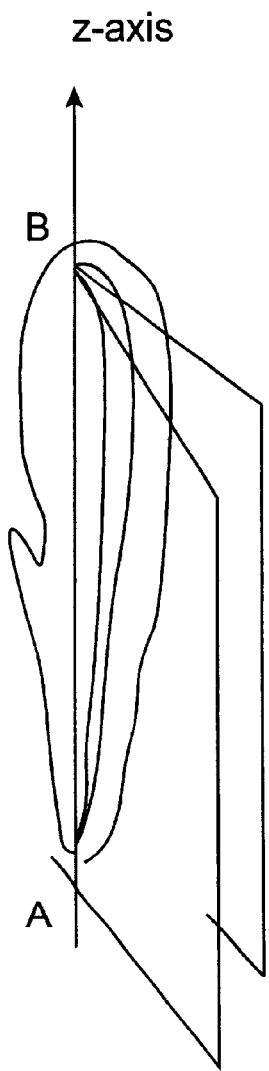
FIGS. 6C and 6D are exemplary diagrams illustrating the operation of the process of FIG. 6B on a tooth model.
Figure 6D:

Alternatively, a second process 300 for fitting a curve network to a tooth is shown in FIG. 6B, and exemplary diagrams illustrating the operation of the process 300 on a tooth model are shown in FIGS. 6C and 6D. In FIG. 6B, during the process of creating a separate mesh for each tooth, a tooth basis is created (step 301). The tooth basis has its origin inside the tooth such as in the middle of the tooth. For reference, the z-axis points towards an occlusion surface, the y-axis points to a labial tooth surface, and the x-axis points to a mesial direction.

Next, the process 300 selects the number of meridians M. M can range between 20–40. Also, the process 300 selects the number of points on each meridian N. N is typically ranges between 2/3M to M. A set of M half planes 0, ..., (M−1) is created: each half plane goes through the tooth z-axis, and the plane i forms an angle (2*PI/M)*i with the tooth x-axis (step 302). Exemplary half planes are shown in FIG. 6C.

For each half plane, an intersection with the tooth mesh surface is determined (step 304. This intersection is a polyline that goes from the lower intersection of z-axis with the tooth surface to their upper intersection (points A and B). This line is called a meridian line.

For each meridian line, a length L is determined and S is determined as a function of L/(N−1) (step 306). From a starting point, the process 300 proceeds along the meridian line and find points p0=A, p1, ..., p[N−1]=B such that the point p[n+1] is at the distance S from p[n] along the meridian. Eventually, an M*N list of points in 3D space is generated and saved (step 308). The points can be saved as short integer values rather than floating point values.

The data is saved and sent to a treating professional. To reconstruct a surface, the grid of M by N points is used to generate a surface that closely resembles a tooth. Although is used in one embodiment, other values for M or N can be 30 or 40.

To reconstruct a surface from a M*N grid of points, a Hermit spline is specified that maps a rectangle [0, M]*[0, N] in (u, v) parameter plane into 3D space. The Hermit spline is a bicubic 3D function on each [m, m+1]*[n, n+1] square in parameter plane. The Hermit spline F is a smooth continued function on the [0, M]*[0, N] rectangle. When restricted to any [m, m+1]*[n, n+1] unit square, the spline is a bicubic 3D function. The restriction of F onto [m, m+1]*[n, n+1] square is denoted by f (omitting the indices (m, n) that should signify that functions f are different on different squares).

The function forms a continuous smooth function on the [0, M]*[0, N] rectangle.

To determine a Hermit spline, 3D values F, two derivatives dF/du, dF/dv, and the second mixed derivative d2F/dudv in each nod point (m, n). Thus for each bicubic function f on [m, m+1]*[n, n+1] square, 3D values f, two derivatives df/du, df/dv, and the second mixed derivative d2f/dudv are generated for the four square corners (m, n), (m+1, n), (m, n+1), (m+1, n+1). A unique 3D bicubic function is completely determined by those values. The bicubic functions on the next squares are smoothly connected because the values and derivatives are the same on the common side.

The 3D values F, two derivatives dF/du, dF/dv, and the second mixed derivative d2F/dudv in the nod points (m, n) are specified as follows:

F(m, n)=(m, n)–th grid point P(m, n);
dF/du(m, n)=0.5*(P(m+1, n)−P(m−1, n));
dF/dv(m, n)=0.5*(P(m, n+1)−P(m, n−1);
d2F/dudv(m, n)=0.

After the Hermit spline on the rectangle [0, M]*[0, N] is determined, its values in the more dense grid of points K*L are computed to derive a K*L grid of 3D points. Each of the four points (k, l), (k+1, k), (k, l+1), (k+1, l+1) are associated with two triangles: {(k, l), (k+1, k), (k, l+1)} and {(k, l+1), (k+1, l+1), (k, l)}. In this way, 2*K*L triangles are generated that are then rendered as a reconstructed tooth.

Figure 7:
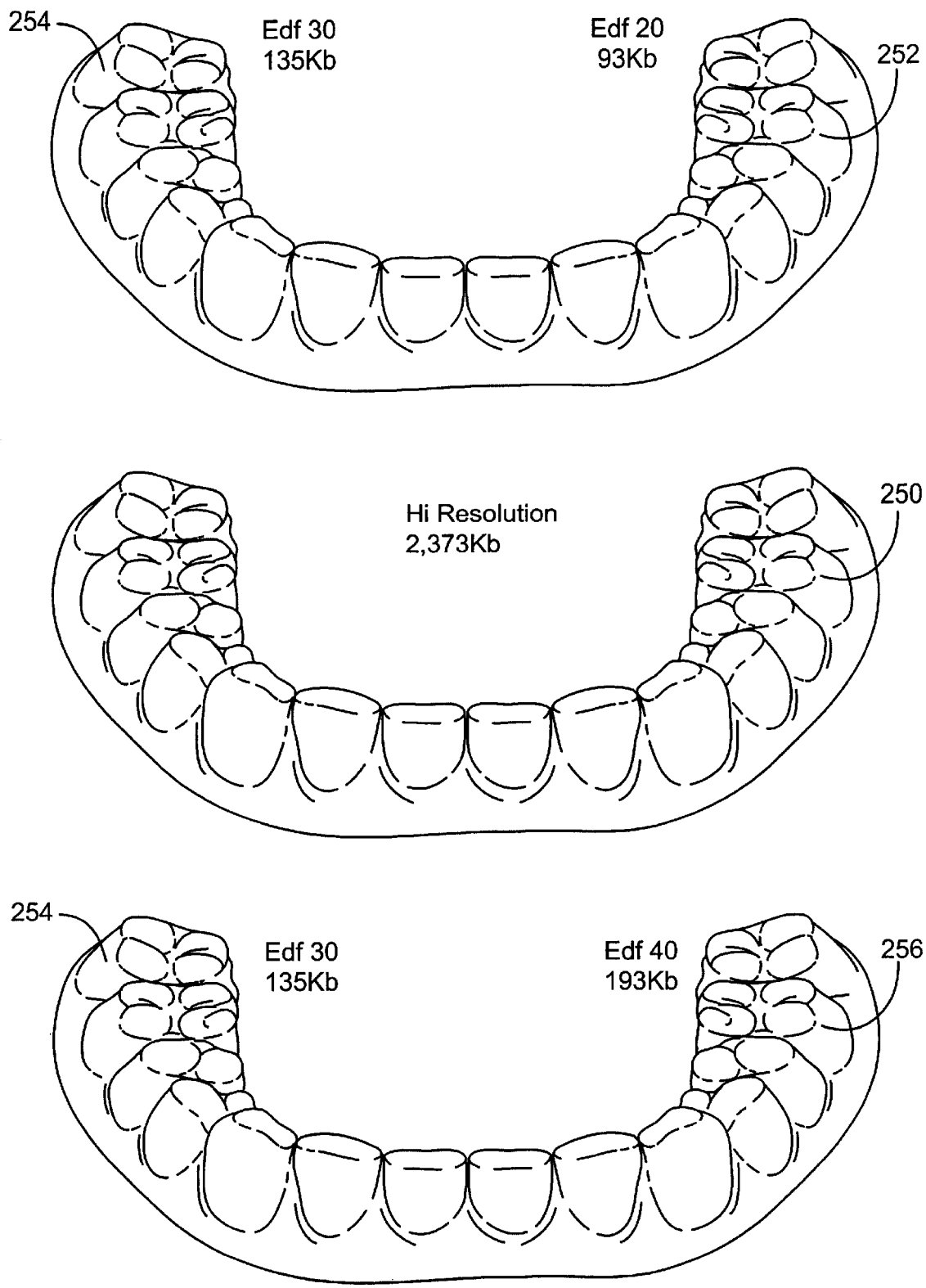
FIG. 7 shows an original high-resolution teeth model and various compressed versions of the teeth model using the processes of FIGS. 5–6.

FIG. 7 shows an original high-resolution nodel 250 of a group of lower teeth and various compressed models of the high-resolution model of the teeth. The original high-resolution model requires 2.373 megabytes of data. In comparison, a 20×20 model 252 requires 93 kilobytes, a 30×30 model 254 requires 135 kilobytes, and a 40×40 model requires 193 kilobytes. The reduction in the size of the file reduces the storage as well as transmission requirements while maintaining good quality. At least one orthodontist had noted that the 30×30 model is, for his application, as good as the original high resolution nodel 250 in developing a treatment plan.

Figure 8:
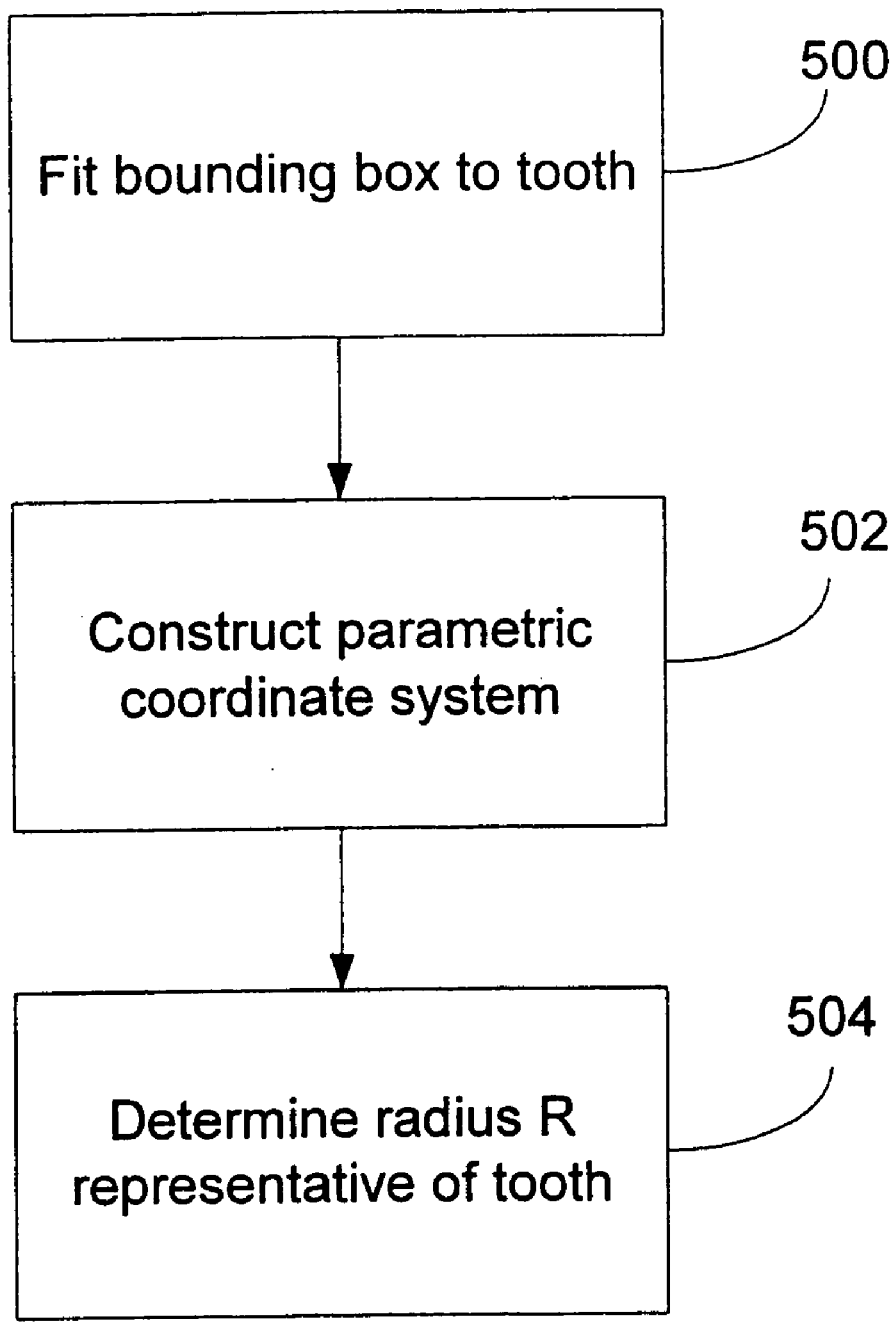
FIG. 8 shows a second embodiment of a system to represent a tooth model using a parametric coordinate system.

FIG. 8 shows another embodiment that uses a curved coordinate system to perform parametric (ϕ, θ, r) to 3D transformations. The process first fits a box into a tooth (step 500). The fitting of the box allows parameters of the curved coordinate system to be determined more accurately.

A parametric coordinate system is constructed (step 502). The coordinate system specifies the conversion of a point P(ϕ, θ, r) into 3D space. Φ ranges from 0 to 2π; θ ranges from 0 to π; and r ranges from 0 to positive infinity.

The phi theta φ, θ space is represented as a regular grid. The step of the grid is determined using the following formulas d_φ=2*π/φ_Resolution and d_θ32 π/θ_Resolution.

In general, the coordinate system can be specified using other parameters, and should satisfy several requirements:
1. The coordinates should parameterize the entire 3D space, or the 3D space except a small set inside the tooth.
2. Curves phi const and theta=const should be linear functions of R (rays). The following formula must be used V(x,y,z)=P(phi, theta)+R*Dir(phi, theta).
3. Coordinate system should provide one-to-one mapping so that rays for different phi and theta do not intersect.
4. Solution should account for different types of teeth.
5. Coordinate system should be simple enough to implement inverse transformation, from 3D space to parametric coordinates. It's desired that sets phi=const be planes.

In one embodiment, the (φ, θ, r)->3D transformation is done with the following equations:

phi ∈[0, 2π].

theta ∈[0, π];

R ∈[0, positive infinity).

V(x, y, z)=P(phi, theta)+R*Direction(phi, theta)

P and Direction functions should be selected to minimize the deviation between the original tooth model and the parametric surface. The formulas for P and Direction may be different for incisors and molars. In one embodiment, the formulas are as follows:
1. For incisor teeth P.x=0;

P.y=YSize*sin(phi);

p.z=ZSize*(1−2*theta/Pi);

Direction.x=sin(theta)*cos(phi);

Direction.y=sin(theta)*sin(phi);

Direction.z=cos(theta);

For molars and other types of teeth:

P.x=XSize*sin(theta)*[1+sin²(2phi)]cos(phi);

P.y=YSize*sin(theta)*[1+sin²(2phi)]sin(phi);

p.z=ZSize*(1−2*theta/Pi);

Direction.x=sin(theta)*cos(phi);

Direction.y=sin(theta)*sin(phi);

Direction.z=cos(theta);

Additionally, a radius R representative of the tooth is constructed (step 504). The radius determination is shown in more detail in FIG. 9.

Figure 9:
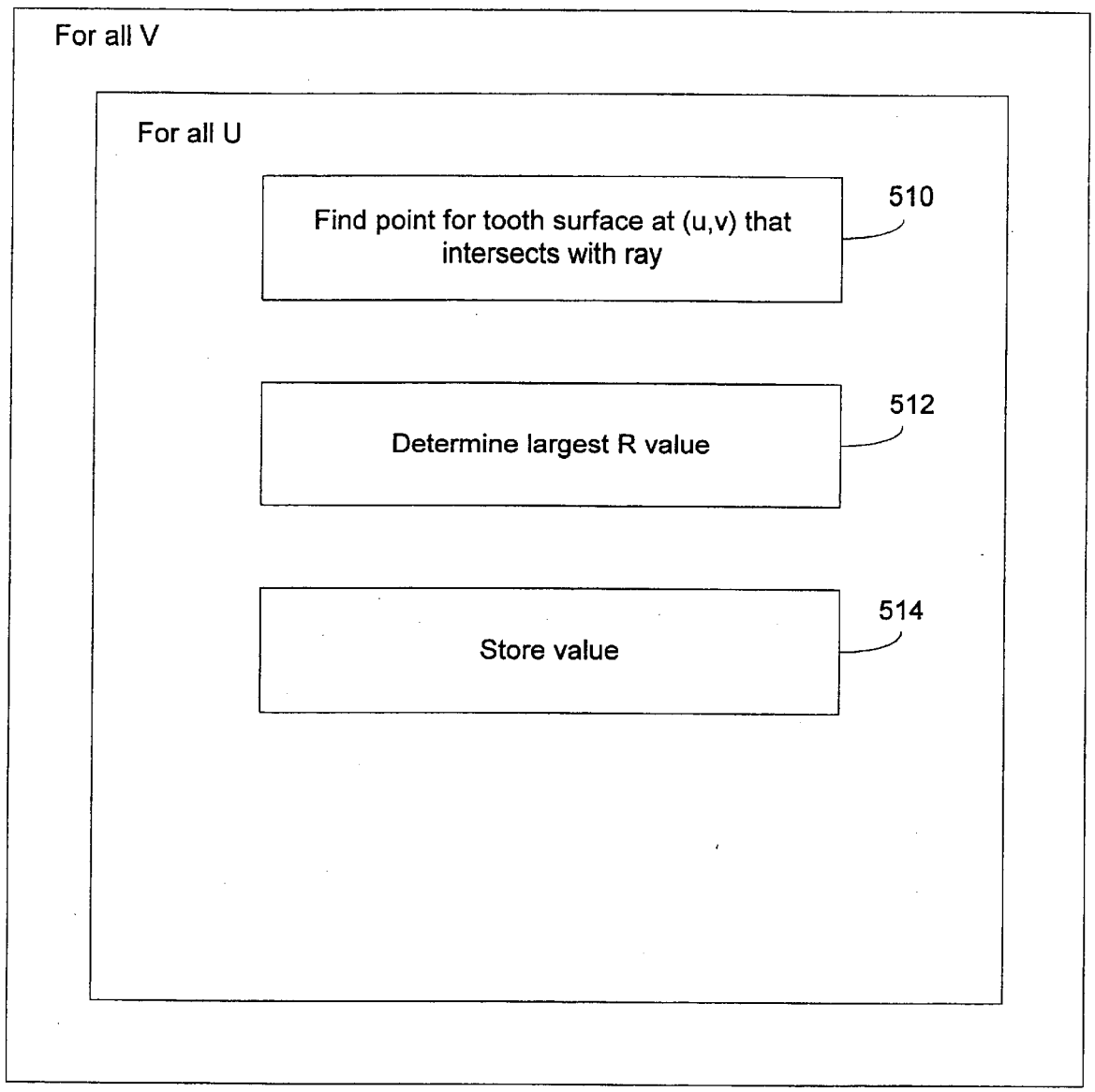
FIG. 9 shows a process for determining a value representative of a tooth.

The process of FIG. 9 determines R by stepping through each phi and each theta on the grid in the PhixTheta space and computes the following. First, the process determines a point on the tooth surface at the point P (φ, θ) that intersects with a ray originating at P aiming at a destination direction specified by Direction (step 510).

Next, the process of FIG. 9 determines the largest R-value for all points of intersection of the ray with the tooth (step 512). The value determined in step 512 is stored in an a table (step 514), and the process is iterated until all phi and theta values have been processed. In one embodiment, for each value stored in the nodes of Phi x Theta grid, only one byte of data is saved to disk. Minimum and maximum values of R are computed. The interval [minR, maxR] is divided into 225 parts. Any R may be approximated using the following formula BYTE b=(BYTE)(255*(R−min)/(maxR−minR));

Since maxR−minR is approximately 5–6 mm for human teeth, the error introduced by this formula is 5/255 mm=0.02 mm.

The collision detection or the determination of the intersection line between two surfaces is efficient. During this process, the embodiment computes the elevation of all grid points in one tooth surface over the other one. If two next points in the grid have different sign elevations, then the segment connecting these points intersects the surface. The segment is approximately divided by the surface into parts proportional to the elevation in its ends. The intersection points on the sides of one grid cell may be connected according to the elevation signs in the vertices to generate an intersection line. This embodiment may be speeded up by first computing elevation values for sub-grid (2*2 or 3*3) of points.

In some applications, tooth penetration may be estimated as the maximum of (minus) elevation of the grid points having a negative elevation. In other applications the penetration may be estimated as (minus) sum of negative elevation. Also, each negative elevation may be multiplied by the cell area. In the latter case, the result is equivalent to the volume of the 3D bodies intersection. Due to the geometry representation, certain minor collisions with small penetrations (smaller than the treatment precision) may occur and these small collisions are ignored by the system.

Given a cell size and the angle between cells, the system can estimate how much a tooth may penetrate into another tooth if all its vertices are outside. The penetration may be significant only if there is a sharp outer angle. When the vertices are found with a small elevation, the mesh in those elevated areas are subdivided. (This is similar to starting with 3*3 mesh, and taking a smaller mesh in close areas only.)

When a user drags a tooth model to move it, teeth penetrations are approximately computed, without subdivisions. When a user releases the tooth model, the penetration can be computed more precisely. If a collision exists, the tooth can be moved a small distance to avoid collision.

The teeth penetration and "distance" (positive elevation) between two teeth are estimated quickly. When the tooth movements are small, the elevation is approximately proportional to the tooth movement (the functions are locally linear), so a touching position (a position with zero elevation) can be determined quickly.

Pseudo-code for the processes of FIGS. 8 and 9 is shown below:
EDF2 ConvertTooth (tooth, resolutionPhi, resolutionTheta
{
    Construct the biggest box that is inside the tooth in the current basis. The box sides must be parallel to coordinate planes (XY, YZ and XY). Move the center of the coordinate system to the center of the box.

Use the sides of the bounding box to construct the parameters of the coordinate system.

$X$Size=0.8*(Box.getMax( ).$x$–Box.getMin( ).$x$)/4;

$Y$Size=0.8*(Box.getMax( ).$y$–Box.getMin( ).$y$)/4;

$Z$Size=0.8*(Box.getMax( ).$z$–Box.getMin( ).$z$)/4;

Sometimes XSize may be made equal to YSize and to min(XSize, YSize). This ensures that the set of 3D points "phi=const" is a plane.

For(theta=0; theta<resolutionTheta; theta++)
{
  For(phi=0; phi<resolutionPhi; phi++)
  {
    1. Find a point on the tooth surface that intersects with the ray for given u and v.
    2. Using that point calculate the R value.

$$R=\|\text{Point}-P(\phi, \theta)\|, \text{ using formula} \quad (1)$$

Since the ray may intersect the surface in more than one point, select the point with the largest R to not make the tooth smaller. This situation should not happen at all, if the coordinate system is "good" for the tooth, but it happens sometimes in small cavities or in cut regions.
    3. Store that value in the table.
  }
}

The processes of FIGS. 8–9 parameterize substantially all 3D space, less a small region inside the tooth. The result is a computationally simple formula that performs (u,v,r)->3D. The inverse mapping 3D->(u,v,r) should also exist and should not involve much computation as well. The process represents the surface in parametric coordinates as an explicit smooth function (smooth—continuous first derivatives) of phi an theta, such as R=F(phi, theta). The compression reduces disk space requirement and increases transmission speed to a clinician.

Moreover, for every 3D point P, the system can easily detect whether the point is inside the tooth for a fast collision detection. It can be accomplished in the following way:

1. Convert P into parametric form (phi, theta, R).
2. For the above phi and theta find Rt of the tooth surface, for example, using bilinear interpolation.
3. If R>Rt, the point is outside the tooth.

Although the above parametric techniques can be used to compress the storage size of a mesh model of a tooth, other techniques can be used. In another embodiment, decimation operations can be applied to the mesh of teeth to eliminate data points, which improves processing speed. After the smoothing and decimation operation have been performed, an error value is calculated based on the differences between the resulting mesh and the original mesh or the original data, and the error is compared to an acceptable threshold value. The smoothing and decimation operations are applied to the mesh once again if the error does not exceed the acceptable value. The last set of mesh data that satisfies the threshold is stored as the tooth model.

Additionally, the mesh model can be simplified by removing unwanted or unnecessary sections of the model to increase data processing speed and enhance the visual display. Unnecessary sections include those not needed for creation of the tooth-repositioning appliance. The removal of these unwanted sections reduces the complexity and size of the digital data set, thus accelerating manipulations of the data set and other operations. After the user instructs the software to erase unwanted sections, all triangles within the box set by the user are removed and the border triangles are modified to leave a smooth, linear border. The software deletes all of the triangles within the box and clips all triangles that cross the border of the box. This requires generating new vertices on the border of the box. The holes created in the model at the faces of the box are retriangulated and closed using the newly created vertices.

In alternative embodiments, the computer automatically simplifies the digital model by performing the user-oriented functions described above. The computer applies knowledge of orthodontic relevance to determine which portions of the digital model are unnecessary for image manipulation.

In another embodiment, data associated with the 3D model includes features can be compressed based on observed characteristics of the tooth surfaces. For example, the system can use the curvature of a particular molar between the tips of the cusps and the gumline to predict the shape of the roots for that molar. Models of typical root and crown shapes also can be used to provide predict the shape of the tooth. The information used to arrive at the predicted shapes can be used in lieu of the original data, thus effecting data compression.

Other feature detection techniques use databases of known cases or statistical information against which a particular 3D image is matched using conventional image pattern matching and data fitting techniques. One such technique, known as "Maximum a posteriori" (MAP), uses prior images to model pixel values corresponding to distinct object types (classes) as independent random variables with normal (Gaussian) distributions whose parameters (mean and variance) are selected empirically. For each class, a histogram profile is created based on a Gaussian distribution with the specified mean and variance. The prior images supply for each pixel and each class the probability that the pixel belongs to the class, a measure which reflects the relative frequency of each class. Applying Bayes' Rule to each class, the pixel values in the input image are scaled according to the prior probabilities, then by the distribution function. The result is a posterior probability that each pixel belongs to each class. The Maximum a posteriori (MAP) approach then selects for each pixel the class with the highest posterior probability.

Once downloaded to a remote workstation, a treating clinician is able to view a patient's treatment plan and alter or comment on the plan. The client viewer application is implemented in a computer program installed locally on a client computer at the clinician's site. In one implementation, the viewer program downloads a data file from a remote host, such as a file transfer protocol (FTP) server maintained by the treatment plan designer, which can be accessed either through direct connection or through a computer network, such as the World Wide Web. The viewer program uses the downloaded file to present the treatment plan graphically to the clinician. The viewer program also can be used by the treatment plan designer at the host site to view images of a patient's teeth.

3-D images of various orthodontic views can then be rendered after the compressed data of the teeth has been received. In this process, an origin point, or "look from" point associated with a camera view is generated. Next, a "look at" point or a focus point associated with the camera view is determined. In this system, the line from LookFrom- Point to LookAtPoint defines the direction the camera is shooting at. Additionally, a camera Z vector, or up vector, is determined.

Pseudo code for generating various orthodontic views is shown below. With reference to the pseudo code, the code defines a boundingbox of one mold (2 arches) which is the smallest cube containing the molds geometry. Other settings associated with the bounding box include:

Z_Axis: point from lower to upper,
Y_Axis: point from inside mouse to front teeth (incisors)
X_Axis: point from center to left.
FieldOfView: is the open angle, it corresponding to lens
HalfFieldOfView: FieldOfView*0.5
MoldCenter: Center of the BoundingBox
X_Length: BoundingBox X dimension
Y_Length: BoundingBox X dimension
Z_Length: BoundingBox X dimension
X_MIN: minimum X value of the BoundingBox i.e. right most surface cube X value.
X_MAX: maximum X value of the BoundingBox
Y_MIN: minimum Y value of the BoundingBox
Y_MAX: maximum Y value of the BoundingBox
Z_MIN: minimum Z value of the BoundingBox
Z_MAX: maximum Z value of the BoundingBox

Right Buccal Overjet

CameraLookFromPoint:
  X=0.5*MoldCenter.X+0.5*X_Max+0.25*MAX(Y_Length, Z_Length)/tan(HalfFieldOfView);
  Y=MoldCenter.Y
  Z=MoldCenter.Z−0.25*MAX(Y_Length, Z_Length)/tan(HalfFieldOf View);
CameraLookAtPoint:
  X=MoldCenter.X+0.25*X_Length;
  Y=MoldCenter.Y;
  Z=MoldCenter.Z;
CameraUpVector: ZAxis;

Anterior Overjet

CameraLookFromPoint:
  X=MoldCenter.X;
  Y=0.5*MoldCenter.Y+0.5*Y_Max+0.25*MAX(X_Length, Z_Length)/tan(HalfFieldOfView);
  Z=MoldCenter.Z−0.25*MAX(X_Length, Z_Length)/tan(HalfFieldOfView);
CameraLookAtPoint:
  X=MoldCenter.X;
  Y=MoldCenter.Y+0.25*Y_Length;
  Z=MoldCenter.Z;
CameraUpVector: ZAxis;

Left Buccal Overjet

CameraLookFromPoint:
  X=0.5*MoldCenter.X+0.5*X_Min−0.25*MAX(Y_Length, Z_Length)/tan(HalfFieldOfView);
  Y=MoldCenter.Y;
  Z=MoldCenter.Z−0.25*MAX(Y_Length, Z_Length)/tan(HalfFieldOf View);
CameraLookAtPoint:
  X=MoldCenter.X−0.25*X_Length;
  Y=MoldCenter.Y;
  Z=MoldCenter.Z;
CameraUpVector: ZAxis;

Left Distal_Molar

CameraLookFromPoint:
  X=MoldCenter.X−0.25*X_Length;
  Y=Y_Min−0.25*MAX(X_Length, Z_Length)/tan(HalfFieldOfView);
  Z=MoldCenter.Z;
CameraLookAtPoint:
  X=MoldCenter.X−0.25*X_Length;
  Y=MoldCenter.Y;
  Z=MoldCenter.Z;
CameraUpVector: ZAxis;

Left Lingual

CameraLookFromPoint:
  X=MoldCenter.X+0.125*X_Length;
  Y=MoldCenter.Y;
  Z=MoldCenter.Z;
CameraLookAtPoint:
  X=MoldCenter.X−0.25*X_Length;
  Y=MoldCenter.Y;
  Z=MoldCenter.Z;
CameraUpVector: ZAxis;

Lingual Incisor

CameraLookFromPoint:
  X=MoldCenter.X;
  Y=MoldCenter.Y;
  Z=MoldCenter.Z;
CameraLookAtPoint:
  X=MoldCenter.X;
  Y=MoldCenter.Y+0.25*Y_Length;
  Z=MoldCenter.Z;
CameraUpVector: ZAxis;

Right Lingual

CameraLookFromPoint:
  X=MoldCenter.X+0.125*X_Length;
  Y=MoldCenter.Y;
  Z=MoldCenter.Z;
CameraLookAtPoint:
  X=MoldCenter.X+0.25*X_Length;
  Y=MoldCenter.Y;
  Z=MoldCenter.Z
CameraUpVector: ZAxis;

Right Distal Molar

Figure 10:
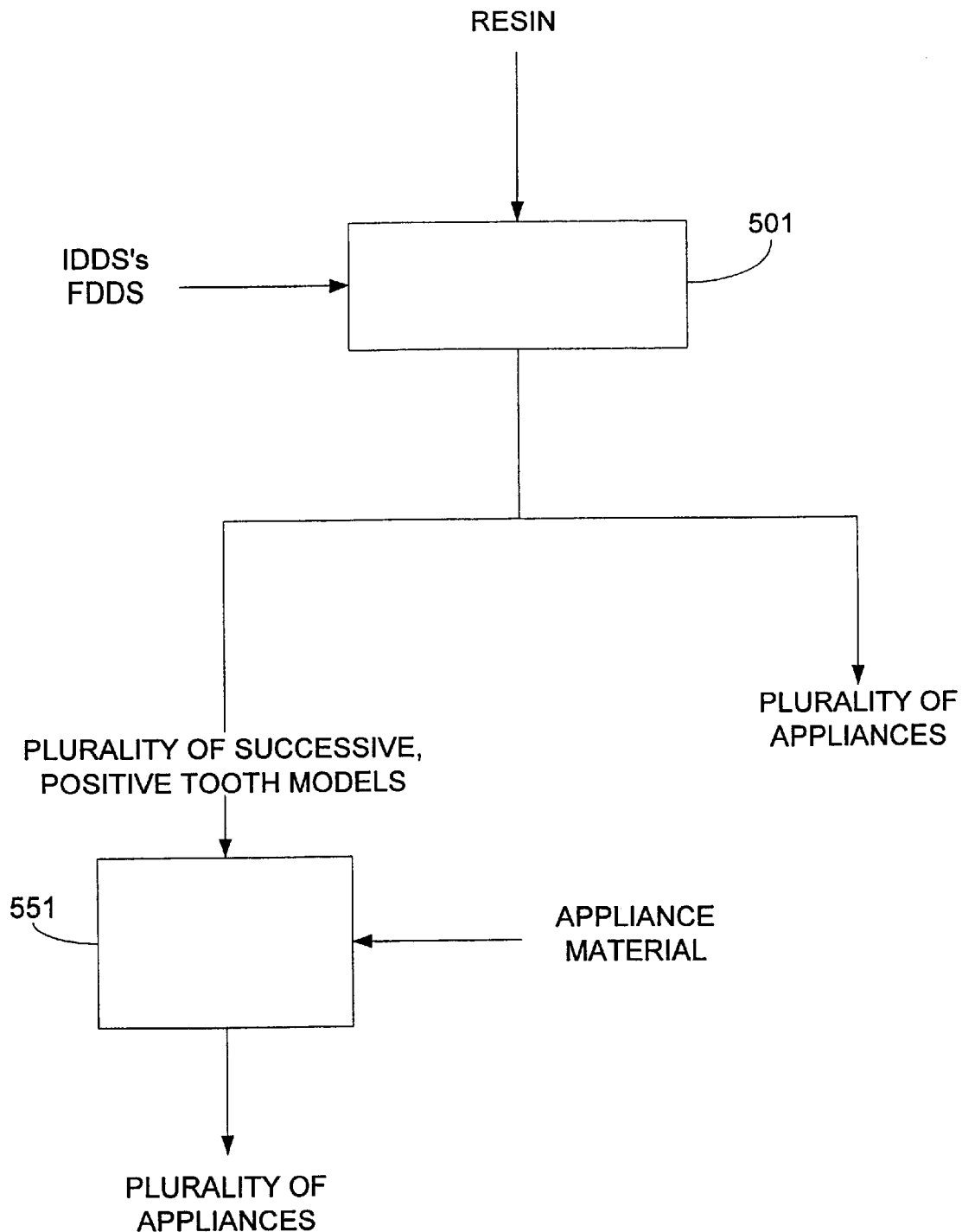
FIG. 10 shows a diagram of a system for fabricating appliances.

CameraLookFromPoint:
  X=MoldCenter.X+0.25*X_Length;
  Y=Y_MIN−0.25*MAX(X_Length, Z_Length)/tan(HalfFieldOfView);
  Z=MoldCenter.Z;
CameraLookAtPoint:
  X=MoldCenter.X+0.25*X_Length;
  Y=MoldCenter.Y;
  Z=MoldCenter.Z;
CameraUpVector: ZAxis;

Once the intermediate and final data sets have been created and reviewed by an orthodontist or suitably trained person, the appliances may be fabricated as illustrated in FIG. 10. Common fabrication methods employ a rapid prototyping device 501 such as a stereolithography machine. A particularly suitable rapid prototyping machine is Model SLA-250/50 available from 3D System, Valencia, Calif. The rapid prototyping machine 501 selectively hardens a liquid or other non-hardened resin into a three-dimensional structure which can be separated from the remaining non-hardened resin, washed, and used either directly as the appliance or indirectly as a mold for producing the appliance. The prototyping machine 501 receives the individual digital data sets and produces one structure corresponding to each of the desired appliances. Generally, because the rapid prototyping machine 501 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine is used to produce the appliances from a more suitable material, such as 0.03 inch thermal forming dental material, available from Tru-Tain Plastics, Rochester, Minn. 55902. Suitable pressure molding equipment is available under the trade name BIO-STAR from Great Lakes Orthodontics, Ltd., Tonawanda, N.Y. 14150. The molding machine 551 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 11:
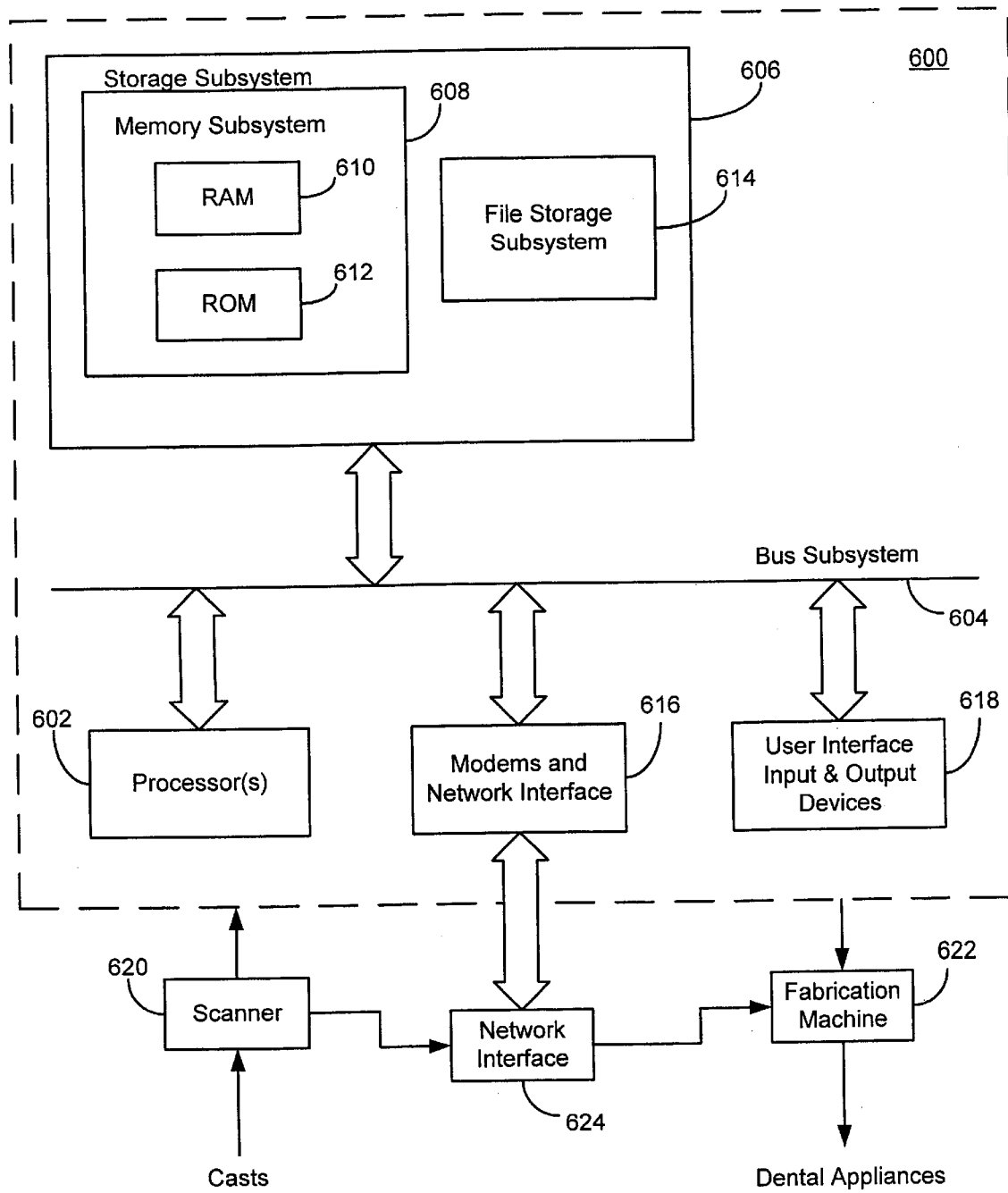
FIG. 11 is a block diagram of a data processing system to develop orthodontic treatment plans.

FIG. 11 is a simplified block diagram of a data processing system 600 that may be used to develop orthodontic treatment plans. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touch-pad, or graphics tablet, or a direct pointing device such as a touch-screen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 606 maintains the basic required programming and data constructs. The program modules discussed above are typically stored in storage subsystem 606. Storage subsystem 606 typically comprises memory subsystem 608 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus sub-system" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624.

Fabrication machine 622 fabricates dental appliances based on intermediate and final data set information received from data processing system 600. In a distributed environment, fabrication machine 622 may be located at a remote location and receive data set information from data processing system 600 via network interface 624.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

What is claimed is:

1. A computer-implemented method for generating a computer model of one or more teeth, comprising:

receiving as input a digital data set of meshes representing the teeth;

selecting a curved coordinate system with mappings to and from a 3D space; and generating a function in the curved coordinate system to represent each tooth;

wherein the coordinate system is based on the following equation:

$$V = P(\phi, \theta) + R^* \text{Direction}(\phi, \theta)$$

where V is the corresponding point in three-dimensional (3D) space to ($\phi$, $\theta$, r), P and Direction are a vector functions expressed in terms of $\phi$ and $\theta$.

2. The method of claim 1, further comprising displaying the computer model of the teeth using the function and the coordinate system.

3. The method of claim 1, further comprising storing a compact coordinate system description and the function in a file representing a compressed version of the digital data set.

4. The method of claim 3, further comprising transmitting the file to a remote computer.

5. The method of claim 4, further comprising displaying the computer model of the teeth using the function at the remote computer.

6. The method of claim 4, wherein the file is transmitted over a network.

7. The method of claim 6, wherein the network is a wide area network.

8. The method of claim 6, wherein the network is the Internet.

9. The method of claim 1, wherein the P and Direction functions are selected to minimize the deviation between the tooth model and a parametric surface specified by the curved coordinate system and the function.

10. The method of claim 1, wherein P and Direction are different for incisors and molars.

11. The method of claim 1, further comprising determining a radius value.

12. The method of claim 1, further comprising receiving an instruction from a human user to modify the graphical representation of the teeth and modifying the graphical representation in response to the instruction.

13. The method of claim 12, further comprising modifying the selected data set in response to the instruction from the user.

14. The method of claim 12, further comprising allowing a human user to select a tooth in the graphical representation and, in response, displaying information about the tooth.

15. The method of claim 12, wherein rendering the graphical representation comprises rendering the teeth at a selected one of multiple viewing orthodontic-specific viewing angles.

16. The method of claim 12, further comprising providing a user interface through which a human user can provide text-based comments after viewing the graphical representation of the teeth.

17. The method of claim 12, wherein rendering the graphical representation comprises downloading data to a remote computer at which a human view wishes to view the graphical representation.

18. The method of claim 1, further comprising delivering data representing the positions of the teeth at selected points along the treatment paths to an appliance fabrication system for use in fabricating at least one orthodontic appliance structured to move the teeth toward the final positions.

19. The method of claim 1, further comprising detecting teeth collision using the curved coordinate system.

20. A computer-implemented method for generating a computer model of one or more teeth, comprising:

receiving as input a digital data set of meshes representing the teeth;

selecting a curved coordinate system with mappings to and from a 3D space; and generating a function in the curved coordinate system to represent each tooth;

receiving an instruction from a human user to modify the graphical representation of the teeth and modifying the graphical representation in response to the instruction; and allowing a human user to select a tooth in the graphical representation and, in response, displaying information about the tooth.

21. The method of claim 20, further comprising displaying the computer model of the teeth using the function and the coordinate system.

22. The method of claim 20, further comprising storing a compact coordinate system description and the function in a file representing a compressed version of the digital data set.

23. The method of claim 22, further comprising transmitting the file to a remote computer.

24. The method of claim 23, further comprising displaying the computer model of the teeth using the function at the remote computer.

25. The method of claim 23, wherein the file is transmitted over a network.

26. The method of claim 25, wherein the network is a wide area network.

27. The method of claim 25, wherein the network is the Internet.

28. The method of claim 20, further comprising determining a radius value.

29. The method of claim 20, wherein rendering the graphical representation comprises rendering the teeth at a selected one of multiple viewing orthodontic-specific viewing angles.

30. The method of claim 20, further comprising providing a user interface through which a human user can provide text-based comments after viewing the graphical representation of the teeth.

* * * * *